(12) United States Patent
Dann et al.

(10) Patent No.: US 9,700,510 B2
(45) Date of Patent: *Jul. 11, 2017

(54) STABILIZED, SPRAYABLE EMULSION CONTAINING ACTIVE AGENT PARTICLES

(71) Applicant: Mission Pharmacal Company, San Antonio, TX (US)

(72) Inventors: Thomas Dann, Oldsmar, FL (US); Renee Nelson, Brandon, FL (US); Brian Wagner, Henderson, NV (US); Mary Walter, Vancouver, WA (US)

(73) Assignee: Mission Pharmacal Company, San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/173,849

(22) Filed: Jun. 6, 2016

(65) Prior Publication Data

US 2016/0279061 A1 Sep. 29, 2016

Related U.S. Application Data

(63) Continuation of application No. 14/619,108, filed on Feb. 11, 2015, now Pat. No. 9,381,156.

(Continued)

(51) Int. Cl.
*A61K 9/12* (2006.01)
*A61K 47/36* (2006.01)
(Continued)

(52) U.S. Cl.
CPC ............ *A61K 9/124* (2013.01); *A61K 9/0014* (2013.01); *A61K 9/107* (2013.01); *A61K 33/30* (2013.01);
(Continued)

(58) Field of Classification Search
None
See application file for complete search history.

(56) References Cited

U.S. PATENT DOCUMENTS 3,770,648 A 11/1973 Mackles
4,981,677 A 1/1991 Thau
(Continued)

FOREIGN PATENT DOCUMENTS

CA 1088428 10/2008
EP 0 531 044 A1 3/1993
(Continued)

OTHER PUBLICATIONS

International Search Report and Written Opinion for PCT/US2015/015316 dated May 18, 2015, 10 pages.

*Primary Examiner* — Aradhana Sasan
(74) *Attorney, Agent, or Firm* — Dority & Manning, P.A.

(57) ABSTRACT

A sprayable emulsion is provided. The emulsion can be used in the treatment of various skin conditions. The emulsion includes a hydrofluoro-based propellant, an emulsification system, an oil phase, a water phase, and active agent particles. Further, the emulsification system includes at least one nonionic emulsifier. The emulsion has a viscosity ranging from about 500 centipoise to about 10,000 centipoise and a hydrophilic to lipophilic balance (HLB) value of from about 2 to about 12. The present inventors have found that by selectively controlling the nature of the emulsification system and the viscosity of the emulsion, the active agent particles resist settling such that a substantially homogeneous distribution of the active agent particles is maintained and can be evenly sprayed onto a surface without running once applied.

29 Claims, 4 Drawing Sheets

Related U.S. Application Data

(60) Provisional application No. 61/939,829, filed on Feb. 14, 2014.

(51) Int. Cl.
    *A61K 9/107*      (2006.01)
    *A61K 47/34*      (2017.01)
    *A61K 47/26*      (2006.01)
    *A61K 47/10*      (2017.01)
    *A61K 9/00*      (2006.01)
    *A61K 33/30*      (2006.01)
    *A61K 47/24*      (2006.01)
    *A61K 47/32*      (2006.01)

(52) U.S. Cl.
    CPC .............. *A61K 47/10* (2013.01); *A61K 47/24* (2013.01); *A61K 47/26* (2013.01); *A61K 47/32* (2013.01); *A61K 47/34* (2013.01); *A61K 47/36* (2013.01)

(56) References Cited

U.S. PATENT DOCUMENTS

| | | |
|---|---|---|
| 5,143,288 A | 9/1992 | Kohler et al. |
| 5,286,475 A | 2/1994 | Louvet et al. |
| 5,871,756 A | 2/1999 | Jeffcoat et al. |
| 6,047,946 A | 4/2000 | Kolanus |
| 6,165,450 A | 12/2000 | Chaudhuri et al. |
| 6,345,775 B1 | 2/2002 | Purvis, II et al. |
| 6,394,321 B1 | 5/2002 | Bayer |
| 6,627,178 B1 | 9/2003 | Cawthon |
| 6,949,249 B2 | 9/2005 | Healy et al. |
| 8,087,548 B2 | 1/2012 | Kimball |
| 8,440,171 B2 | 5/2013 | Valpey, III et al. |
| 8,465,728 B2 | 6/2013 | Tasz et al. |
| 9,381,156 B2 * | 7/2016 | Dann .................... A61K 9/124 |
| 2005/0255048 A1 | 11/2005 | Hirsh et al. |
| 2006/0034937 A1 | 2/2006 | Patel |
| 2006/0165603 A1 | 7/2006 | Meakin et al. |
| 2007/0027213 A1 | 2/2007 | Oberegger et al. |
| 2008/0031907 A1 | 2/2008 | Tamarkin et al. |
| 2008/0194494 A1 | 8/2008 | Martinez et al. |
| 2009/0257957 A1 | 10/2009 | Burnier et al. |
| 2011/0150792 A1 | 6/2011 | Shao et al. |
| 2011/0240683 A1 | 10/2011 | Stegeman |
| 2012/0058973 A1 | 3/2012 | Narasimhan et al. |
| 2013/0058985 A1 | 3/2013 | Willems et al. |
| 2013/0078191 A1 | 3/2013 | Teramoto et al. |
| 2013/0115173 A1 | 5/2013 | Trumbore et al. |
| 2013/0164226 A1 | 6/2013 | Nakamoto |
| 2013/0233310 A1 | 9/2013 | Hilgers et al. |
| 2013/0251644 A1 | 9/2013 | Majhi et al. |
| 2013/0303615 A1 | 11/2013 | Scholz et al. |
| 2015/0231071 A1 | 8/2015 | Dann et al. |
| 2015/0232260 A1 | 8/2015 | Dann et al. |

FOREIGN PATENT DOCUMENTS

| | | |
|---|---|---|
| EP | 0 937 451 A2 | 8/1999 |
| JP | 2000 128773 | 5/2000 |

\* cited by examiner

# STABILIZED, SPRAYABLE EMULSION CONTAINING ACTIVE AGENT PARTICLES

RELATED APPLICATION

The present application is a continuation of U.S. application Ser. No. 14/619,108, filed on Feb. 11, 2015, which claims priority to U.S. Provisional Application Ser. No. 61/939,829, filed on Feb. 14, 2014, both of which are incorporated herein in their entirety by reference thereto.

BACKGROUND OF THE INVENTION

Much of the population has experienced a skin condition such as a rash, a pressure ulcer, a wound such as a cut or first degree burn, an allergic reaction, or any other skin condition that can cause itching, inflammation, pain, or any other type of discomfort that has required topical application of a cream or ointment to assist in the healing process. Often, some of these conditions are more prevalent in infants, the elderly, and infirm. For instance, infants, the elderly, and infirm can be susceptible to developing incontinent dermatitis, which occurs when the skin is exposed to prolonged wetness, increased skin pH caused due to contact with urine and feces, and the resulting breakdown of the stratum corneum, or the outermost layer of the skin. Meanwhile, pressure ulcers, also known as decubitus ulcers or bedsores, are also a concern. Pressure ulcers are localized injuries to the skin and/or underlying tissue that usually occur over a bony prominence as a result of pressure, or pressure in combination with shear and/or friction. The most common sites are the sacrum, coccyx, heels or the hips, but other sites such as the elbows, knees, ankles or the back of the cranium can be affected. Pressure ulcers occur due to pressure applied to soft tissue resulting in completely or partially obstructed blood flow to the soft tissue. Factors that can contribute to the formation of ulcers include protein-calorie malnutrition, microclimate (skin wetness caused by sweating or incontinence), diseases that reduce blood flow to the skin, such as arteriosclerosis, or diseases that reduce the sensation in the skin, such as paralysis or neuropathy.

The aforementioned conditions, and other skin conditions, can be prevented or treated, for instance, by the application of an active agent to the affected area of the skin. Active agents can, for instance, help speed up the wound healing process and can also limit the skin's exposure to excessive moisture. As such, one approach for treating these skin conditions is to block moisture from reaching the skin, such as by the application of oil-based protectants or barrier creams, including various over-the-counter creams or ointments containing moisture barrier active agents, to the affected area. However, if the skin is not thoroughly dry, some of these oil-based protectants and creams can actually seal the moisture inside the skin rather than outside the skin. Further, such protectants and creams are very viscous and can be greasy, resulting in difficulty in removing the protectants and creams from one's hands after application onto the affected area of the skin. In addition, rubbing these products into the skin can cause additional discomfort or pain, and in the event that a caretaker or healthcare provider must apply the product to a patient, this could lead to embarrassment for both the patient and caretaker depending on the location of application.

As such, a need exists for a composition that can provide an even coating of an active agent to the skin that is easier to apply and that does not cause discomfort. One approach is to use an active agent in conjunction with a propellant to create a sprayable composition. However, often the high viscosity of the resulting aerosol spray composition means that it can be difficult to formulate the composition into a medium that can be sprayed due to issues with clogging of the valves and nozzle in the dispenser. Meanwhile, to counteract this problem, other sprayable compositions are formulated to have a low viscosity to allow for spraying, but this can result in compositions that are not viscous enough when applied to the skin's surface, resulting in a runny product that does not evenly coat or effectively contact the skin.

Still another problem associated with the aforementioned sprayable compositions is that the active agents of the sprayable compositions are particulate-based and often settle to the bottom of the container in which the sprayable composition is stored, particularly when the viscosity is low, resulting in caking of the product in the container and the inability to deliver the active agent in a uniform manner.

As such, a need exists for a stable, sprayable composition containing active agent particles that remain substantially homogeneously distributed and that can be evenly sprayed onto the skin as a fine mist.

SUMMARY OF THE INVENTION

In accordance with one embodiment of the present invention, a sprayable emulsion is disclosed. The emulsion includes a hydrofluoro-based propellant, an emulsification system, an oil phase, a water phase, and active agent particles. Further, the emulsification system includes at least one nonionic emulsifier. The sprayable emulsion has a viscosity ranging from about 500 centipoise to about 10,000 centipoise and a hydrophilic to lipophilic balance (HLB) value of from about 2 to about 12.

In accordance with another embodiment of the present invention, a method of forming a sprayable emulsion is disclosed. The method includes forming a base emulsion composition, introducing the base emulsion composition into a spray container, and injecting a hydrofluoro-based propellant into the container. The base emulsion composition includes active agent particles, an emulsification system, an oil phase, and a water phase. Further, the emulsification system includes at least one nonionic emulsifier. In addition, the sprayable emulsion has a viscosity of from about 500 centipoise to about 10,000 centipoise and a hydrophilic to lipophilic balance (HLB) value of from about 2 to about 12.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figure, in which.

Figure 1:
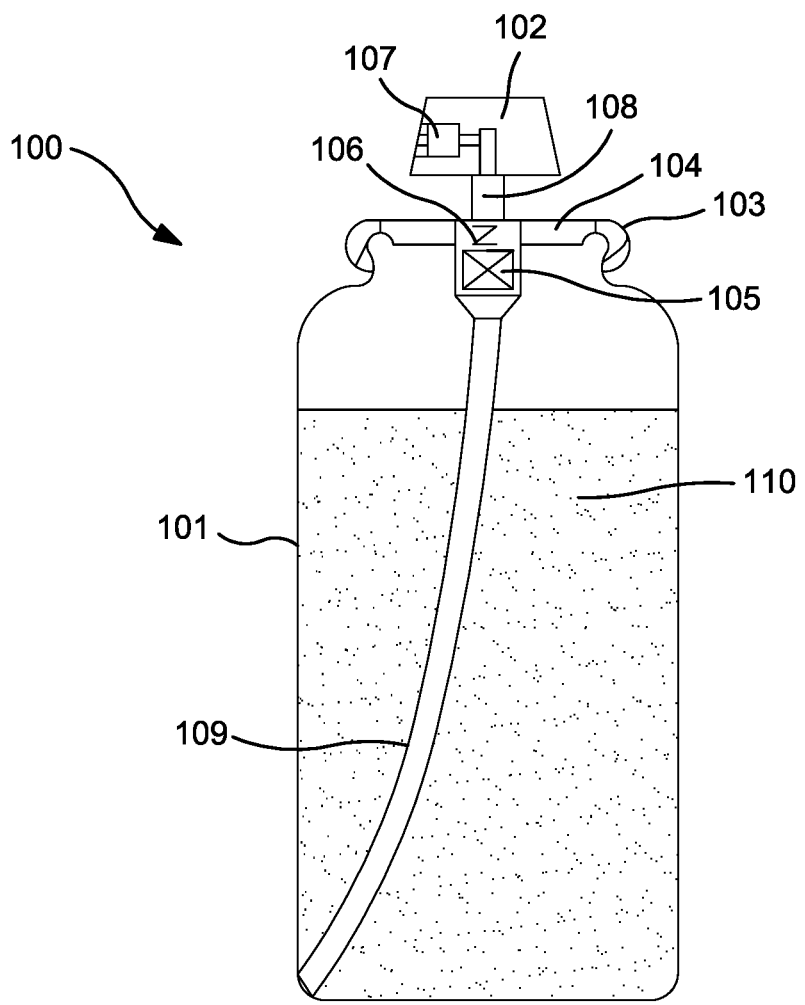
FIG. 1 is a cross-sectional side view of a spray delivery system according to one embodiment of the present disclosure.
Figure 2A:
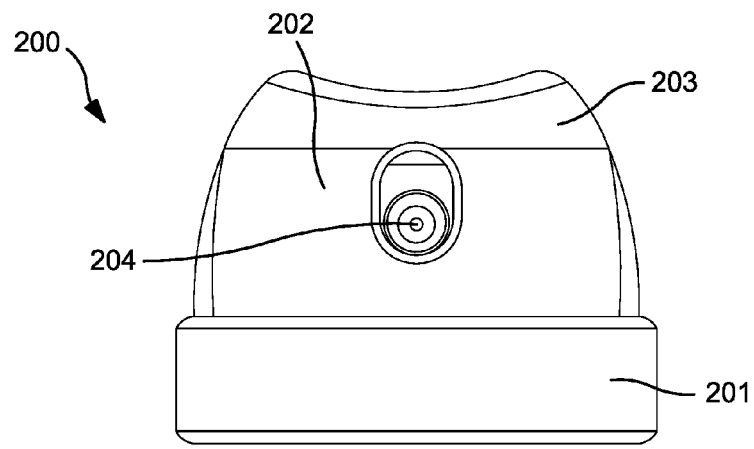
FIG. 2A is front view of an actuator that can be used in a spray delivery system according to one embodiment of the present disclosure.
Figure 2B:
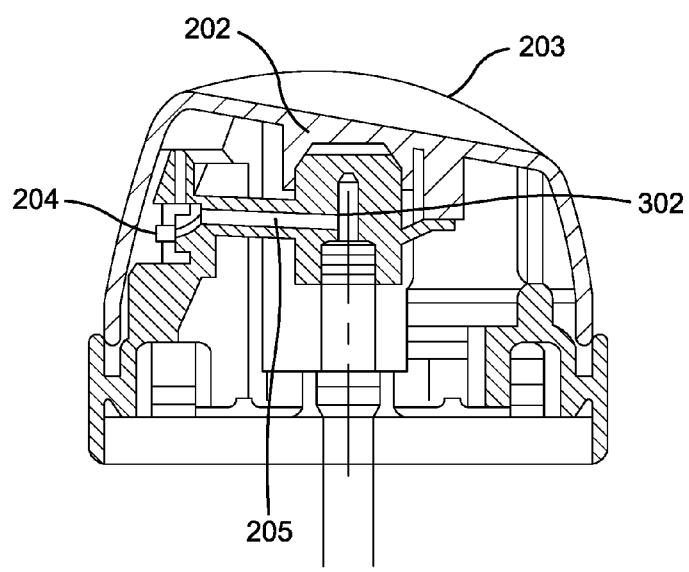
FIG. 2B is a cross-sectional side view of the actuator of FIG. 2A.
Figure 3:
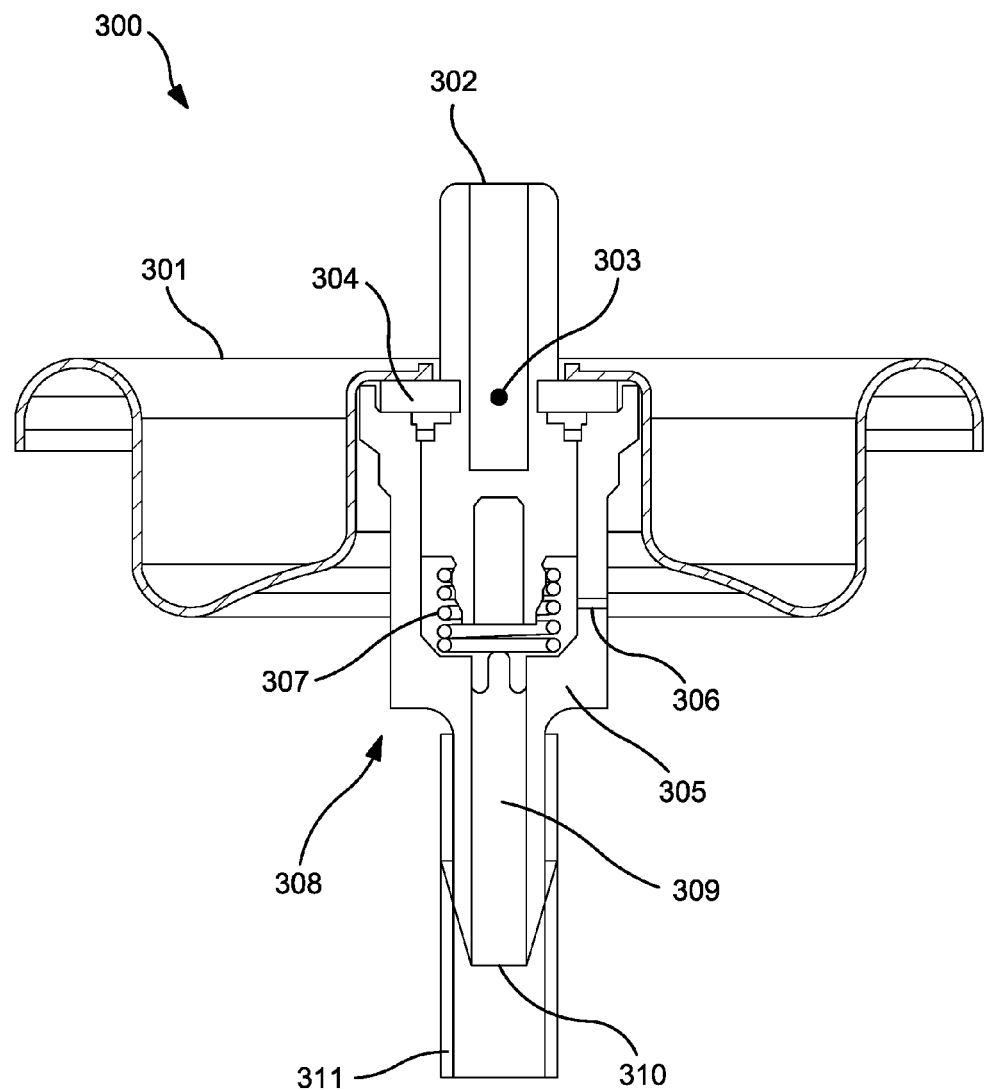
FIG. 3 is a cross-sectional side view of a spray assembly according to one embodiment of the present disclosure.
Figure 4:
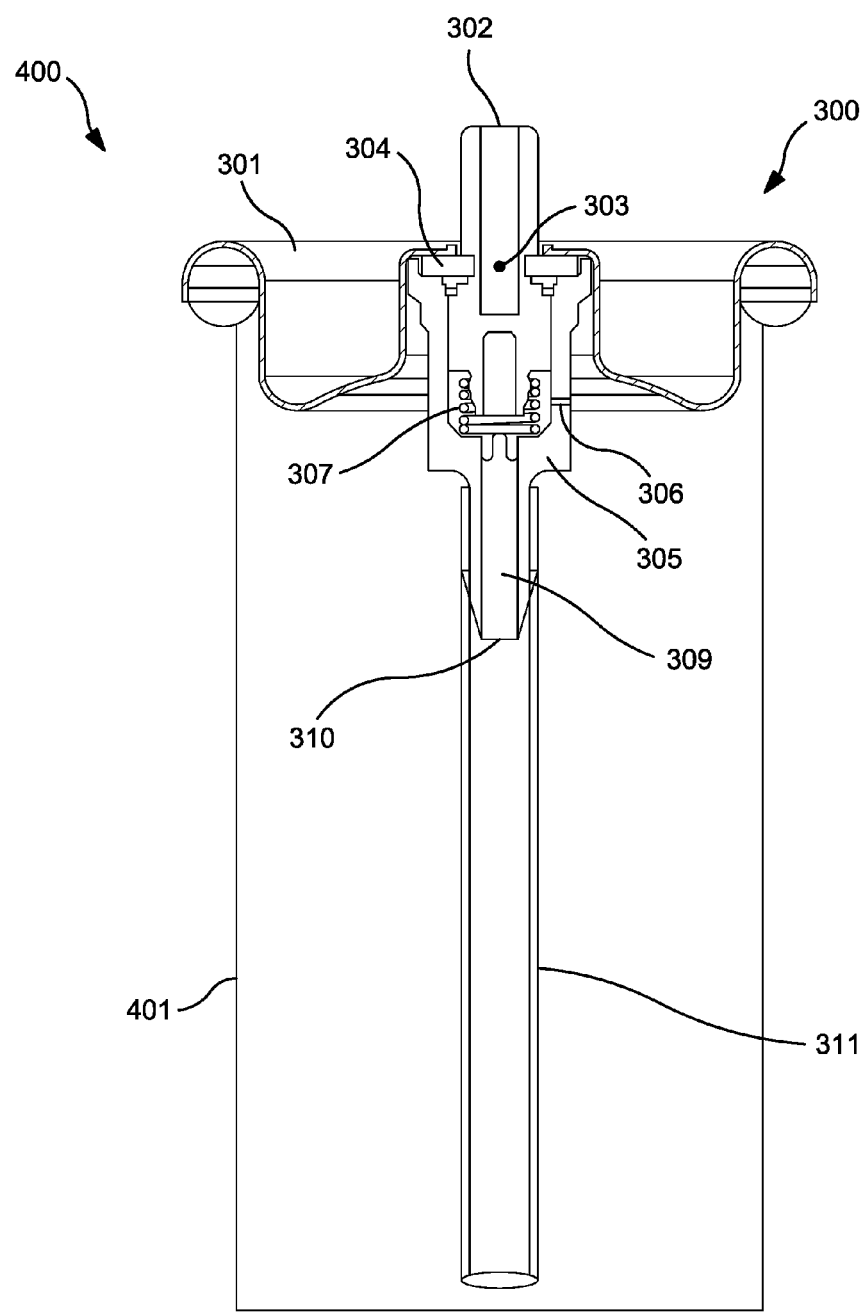
FIG. 4 is a cross-sectional side view of a spray delivery system according to another embodiment of the present disclosure utilizing the spray assembly of FIG. 3.

Repeat use of reference characters in the present specification and drawing is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

Generally speaking, the present invention is directed to a sprayable emulsion that can be used, for example, in the treatment of a skin condition or any other condition where the topical application of an active composition is desired. The emulsion can be used in the treatment of various skin conditions. The emulsion includes a hydrofluoro-based propellant, an emulsification system, an oil phase, a water phase, and active agent particles. Further, the emulsification system includes at least one nonionic emulsifier. The present inventors have found that by selectively controlling the type of propellant used, the nature of the emulsification system, and the viscosity of the emulsion, a sprayable emulsion can be achieved where the active agent particles resist settling such that a substantially homogeneous distribution of the active agent particles is maintained and can be evenly sprayed onto a surface without running once applied. For instance, the sprayable emulsion can be stable such that less than about 3 wt. %, such as less than about 2 wt. %, such as less than about 1 wt. % of the active agent particles in the emulsion settle when stored in a container at 21° C. for 3 days. This results in an emulsion that can be evenly sprayed on a surface as a substantially uniform coating of active agent particles. In addition, the emulsion can have a viscosity ranging from about 500 centipoise to about 10,000 centipoise, such as from about 1000 centipoise to about 8000 centipoise, such as from about 1500 centipoise to about 6000 centipoise, such as from about 2000 centipoise to about 4000 centipoise.

The propellant can be, for instance, a hydrofluoro-based propellant such as a hydrofluoro-olefin or a hydrofluoroalkane. Further, the emulsification system can include at least one nonionic emulsifier. In some embodiments, one or more nonionic lipophilic emulsifiers can be used in conjunction with one or more nonionic hydrophilic emulsifiers such that the ratio of the hydrophilic/lipophilic balance ("HLB") value of the overall sprayable emulsion can range from about 2 to about 12, such as from about 3 to about 10, such as from about 4 to about 9, such as from about 5 to about 8. Meanwhile, the ratio of the lipophilic emulsifiers to the hydrophilic emulsifiers used can range from about 5 to about 30, such as from about 7.5 to about 25, such as from about 10 to about 20.

I. Sprayable Emulsion a. Propellant

The sprayable emulsion of the present invention includes a propellant to provide the energy needed to aid in the delivery of active agent particles to a surface of the skin affected with skin conditions such as rashes, ulcers, cuts, or wounds. In other words, the propellant can provide the propulsive forced needed to spray the active agent particles onto the skin. As such, the propellant has enough dispersive energy to overcome the surface tension of the liquid components of the sprayable emulsion.

The emulsion includes a propellant particularly useful for facilitating the spray of the active agent particles. The present inventors have found that by selectively controlling certain aspects of the propellant, such as the specific gravity, vapor pressure, and/or molecular weight, a composition having a substantially homogeneous distribution of active agent particles can be achieved.

The ratio of the specific gravity of the propellant to specific gravity of the emulsion can range from about 0.7 to about 1.6, such as from about 0.8 to about 1.5, such as from about 0.9 to about 1.4. Such a specific gravity ratio results in the propellant having a specific gravity similar to the overall emulsion, which means that the propellant can be substantially homogeneously distributed throughout the emulsion. Because the propellant is distributed throughout the emulsion in this manner, settling of the active agent particles and other particulates contained in the sprayable emulsion can be prevented. Further, the propellant can have a specific gravity ranging from about 1.03 to about 1.3, such as from about 1.05 to about 1.25, such as from about 1.07 to about 1.2 as determined at 21° C. and based on water having a density of 1.0 at 21° C. Meanwhile, the sprayable emulsion can have a specific gravity of from about 0.8 to about 1.3, such as from about 0.85 to about 1.25, such as from about 0.9 to about 1.2, as determined at 21° C.

In addition, the propellant can provide a high enough vapor pressure to the emulsion such that it can be atomized and sprayed in aerosol form, yet the vapor pressure is not so high that the resulting spray creates excessive misting or discomfort when sprayed onto the skin or requires a specially designed aerosol container. For instance, the vapor pressure at room temperature (21° C.) can be less than about 60 psi. In some embodiments, for example, the vapor pressure can range from about 30 psi to about 60 psi, such as from about 35 psi to about 55 psi, such as from about 40 psi to about 50 psi. Without intending to be limited by theory, it is believed that by using a propellant that has a lower vapor pressure at room temperature compared to other propellants, the propellant can be used in larger amounts in the sprayable emulsion, which results in a smoother, more easily controlled, spray and also ensures complete evacuation of the container in which the sprayable emulsion is stored. Further, because the propellant's low vapor pressure, it is not necessary to use a high pressure aerosol container as is required when utilizing other propellants.

In addition, the molecular weight of the propellant can be greater than 100 grams per mole, such as from about 100 grams per mole to about 400 grams per mole, such as from about 105 grams per mole to about 300 grams per mole, such as from about 110 grams per mole to about 200 grams per mole. By using a propellant having a molecular weight in this range, settling of the active agent particles can be further prevented.

In one embodiment, the propellant can include at least one hydrofluoro-olefin. In one particular embodiment, the propellant includes a hydrofluoro-olefin containing from 3 to 4 carbon atoms, such as three carbon atoms. The hydrofluoro-olefin propellant of the present invention can be referred to as an "HFO" when it contains at least one hydrogen, at least one fluorine and no chlorine. HFOs are derivatives of alkenes. In some embodiments, the HFO propellant can contain two carbon-carbon double bonds.

In one particular embodiment, the sprayable emulsion of the present invention includes a propellant represented by Formula I below:

[Formula I]

$$\begin{array}{c} R \\ \diagdown \\ C = C - R' \\ \diagup \\ R \end{array} \begin{array}{c} R \\ | \end{array}$$

where each R is independently a hydrogen or a halogen such as fluorine (F), bromine (Br), iodine (I), or chlorine (Cl), and preferably fluorine (F), R' is $(CR_2)_nY$,
Y is $CRF_2$, and
n is 0 or 1.

Further, in one particular embodiment, Y is $CF_3$, n is 0, and at least one of the remaining Rs is F. In another particular embodiment, Y is $CF_3$, at least one R on the unsaturated terminal carbon is H, and at least one of the remaining Rs is F. In still other embodiments, the fluoroolefin propellant of the present invention can include one or more tetrafluoropropenes, and such a propellant can be referred to herein as a HFO-1234 propellant. Examples of tetrafluoropropenes contemplated by the present invention are HFO-1234yf (specific gravity of 1.092 at 21° C.) and HFO-1234ze (specific gravity of 1.17 at 21° C.), in the cis- and/or trans-forms. It should be understood that HFO-1234ze refers to 1,1,1,3-tetrafluoropropene, independent of whether it is the cis- or trans-form, and the terms "cisHFO-1234ze" and "transHFO-1234ze" are used herein to describe the cis- and trans-forms of 1,1,1,3-tetrafluoropropene, respectively.

In some embodiments, the HFO-1234ze can include a combination of transHFO-1234ze and cisHFO-1234ze, such as from about 90% to about 99% trans-isomer on the basis of total HFO-1234ze, with the cis-isomer comprising from about 1% to about 10% of the same basis. As such, in some embodiments, the propellant of the present invention can include a combination of cisHFO-1234ze and transHFO-1234ze, preferably in a cis- to trans-weight ratio of from about 1:99 to about 10:99, such as from about 1:99 to about 5:95, such as from about 1:99 to about 3:97.

Although the properties of cisHFO-1234ze and transHFO-1234ze differ in at least some respects, it is contemplated that each of these compounds is adaptable for use, either alone or together with other compounds including its stereoisomer, as a propellant in the sprayable emulsion of the present invention. For example, while transHFO-1234ze has a relatively low boiling point (−19° C.), it is nevertheless contemplated that cisHFO-1234ze, with a boiling point of 9° C., can also be used as a propellant in the sprayable emulsion of the present invention. Further, it is to be understood that the terms HFO-1234ze and 1,1,1,3-tetrafluoropropene refer to both stereo isomers, and the use of these terms covers both the cis- and trans-forms.

Another type of propellant that can be used is a hydrofluoroalkane, which can be referred to as an "HFA." HFA propellants are also known as hydrofluorocarbons or "HFC" propellants. An example of a suitable HFC propellant is 1,1,1,2-tetrafluoroethane, which can also be referred to as HFC-134a. Another type of HFC propellant that can be used is 1,1,1,2,3,3,3-heptafluoropropane, which can also be referred to as HFC-227ea.

Regardless of the particular propellant utilized, the amount of the propellant contained in the sprayable emulsion of the present invention can range from about 5 wt. % to about 95 wt. %, such as from 10 wt. % to about 80 wt. %, such as from about 15 wt. % to about 60 wt. % based on the total weight of the emulsion.

b. Active Agent Particles

The sprayable emulsion of the present invention further includes active agent particles, which can mean any compound or mixture of compounds which produces a physiological result upon contact with a living organism (e.g., a mammal) such as a human. Active agent particles can be distinguishable from other components of the sprayable emulsion, such as preservatives, conditioning agents, emollients, viscosity modifiers, emulsifiers, etc. The active agent particles can include any molecule, as well as a binding portion or fragment thereof, that is capable of modulating a biological process. In some embodiments, the active agent particles can be used in the diagnosis, treatment, or prevention of a disease or as a component of a medication, pharmaceutical, cosmetic, or cosmeceutical. Further, the active agent particles can be compounds that interact with or influence or otherwise modulate a target in a living subject. The target may be a number of different types of naturally occurring structures, where targets of interest include both intracellular and extra-cellular targets. Active agent particles can include, for example, moisture barriers, antifungals, antibacterials, analgesics, antiseptics, anesthetics, anti-inflammatories, antipruritics, etc. The active agent particles can have an average particle size of from about 20 nanometers to about 1000 nanometers, such as from about 25 nanometers to about 500 nanometers, such as from about 30 nanometers to about 250 nanometers.

In one embodiment, the active agent particles can include zinc oxide particles, which repel moisture and create a barrier between the skin and environment to protect the skin from excessive moisture. The zinc oxide particles can have an average particle size of from about 20 nanometers to about 200 nanometers, such as from about 25 nanometers to about 150 nanometers, such as from about 30 nanometers to about 100 nanometers.

The zinc oxide particles can be hydrophobic, for example, by application of a hydrophobic coating on the surface of the zinc oxide particles, as described in more detail below. The particles can also carry an inorganic coating, separately or in combination with the hydrophobic coating, as described in more detail below. The zinc oxide particles may be coated with alumina, silica, an organic material, silicones, or combinations thereof. Other suitable surface treatments may include: phosphate esters (including lecithins), perfluoroalkyl alcohol phosphates, fluorosilanes, isopropyl titanium triisostearate, stearic or other fatty acids, silanes, dimethicone and related silicone polymers, or combinations thereof.

For example, zinc oxide particles may be coated with oxides of other elements such as oxides of aluminum, zirconium or silicon, or mixtures thereof such as alumina and silica. Alternatively, the zinc oxide particles may be treated with boron nitride or other known inorganic coatings, singly or in combinations before incorporation into the voids of the particulate. The inorganic coating may be applied using techniques known in the art. A typical process can include forming an aqueous dispersion of zinc oxide particles in the presence of a soluble salt of the inorganic element whose oxide will form the coating. This dispersion is usually acidic or basic, depending upon the nature of the salt chosen, and precipitation of the inorganic oxide is achieved by adjusting the pH of the dispersion by the addition of acid or alkali, as appropriate. The inorganic coating, if present, can be applied as a first layer to the surface of the zinc oxide particles.

In another embodiment, the zinc oxide particles can include an organic coating that provides hydrophobicity. The organic coating can be applied to the inorganic coating, if present, or directly to the zinc oxide. The hydrophobic coating agent may be, for example, a silicone, a silane, a metal soap, a titanate, an organic wax, or combinations thereof. The hydrophobic coating can alternatively include a fatty acid, for example, a fatty acid containing 10 to 20 carbon atoms, such as lauric acid, stearic acid, isostearic acid, and salts of these fatty acids. The fatty acid may be isopropyl titanium trisostearate. With respect to the silicone, the hydrophobic coating may be a methicone, a dimethicone, their copolymers or mixtures thereof. The silicone may also be an organosilicon compound, for example dimethylpolysiloxanes having a backbone of repeating -Me$_2$SiO— units ("Me" is methyl, $CH_3$), methyl hydrogen polysiloxanes having a backbone of repeating -MeHSiO— units and alkoxysilanes of formula $R_nOSiH_{(4-n)}$ where "R" is alkyl and "n" is the integer 1, 2 or 3. With respect to the silane, the hydrophobic coating agent may be an alkoxysilanes, for example an alkyltriethoxy or an alkyltrimethoxy silanes available from OSI Specialties or PCR. The alkoxysilane may be a triethoxycaprylylsilane or a perfluoroalkylethyl triethoxysilane having a $C_3$ to $C_{12}$ alkyl group that is straight or branched. Zinc oxide particles with a triethoxycaprylylsilane coating are commercially available under the name ZANO™ 10 Plus from Umicore Zinc Chemicals.

Still other active agent particles that can be used in the sprayable emulsion can include paraffin, microcrystalline wax, petrolatum, beeswax, or a combination thereof. Such active agent particles can act as moisture repellant materials.

Regardless of the type of active agent particles utilized, the amount of active agent particles contained in the sprayable emulsion of the present invention can range from about 0.1 wt. % to about 30 wt. %, such as from 1 wt. % to about 25 wt. %, such as from about 2 wt. % to about 20 wt. % based on the total weight of the emulsion.

c. Oil and Water Phases

The sprayable emulsion can also include an oil phase and a water phase. The oil phase and the water phase can form a water-in-oil emulsion or an oil-in-water emulsion. Suitable oils that can be used in the oil phase of the emulsion include mineral oils, plant-based oils, silicone oils, or a combination thereof. Examples of commercially available mineral oils, which are liquid petroleum derivatives that may be used in accordance with the present invention can include Witco Corporation's CARNATION™ mineral oil or Penreco Corporation's DRAKEOL™ mineral oil. Suitable plant-based oils, which are non-petroleum biomass derived oils, that can be used include vegetable or fruit oils, such as almond oil, peanut oil, wheat germ oil, linseed oil, jojoba oil, apricot pit oil, walnut oil, palm nut oil, pistachio nut oil, sesame seed oil, rapeseed oil, cade oil, corn oil, peach pit oil, poppy seed oil, pine oil, castor oil, soybean oil, avocado oil, safflower oil, coconut oil, hazelnut oil, olive oil, grape seed oil, sunflower oil, apricot kernel oil, geranium oil, rice bran oil and mixtures thereof. Silicone oils that can be used include disiloxane, cyclomethicone, dimethicone and derivatives thereof, and polydimethylsiloxane fluids. Cyclomethicone is a volatile compound and evaporates when applied to the skin's surface, such that the resulting coating is drier to the touch. Other similar volatile compounds that can be used include isododecane.

Water can be used in conjunction with any of the oils described above as part of water phase of a water-in-oil emulsion or an oil-in-water emulsion. The water phase can include water alone, or the water phase can include water in addition to one or more water soluble components of the sprayable emulsion.

When an emulsion containing oil and water is formed, the oil can be present in the emulsion in an amount ranging from about 1 wt. % to about 35 wt. %, such as from about 3 wt. % to about 30 wt. %, such as from about 5 wt. % to about 25 wt. % based on the total weight of the emulsion. Meanwhile, the water can be present in an amount less than about 50 wt. %, such as an amount ranging from about 1 wt. % to about 50 wt. %, such as from about 5 wt. % to about 45 wt. %, such as from about 10 wt. % to about 40 wt. % based on the total weight of the emulsion. Further, the total amount of the oil and water phases present in the emulsion can range from about 10 wt. % to about 70 wt. %, such as from about 15 wt. % to about 65 wt. %, such as from about 20 wt. % to about 60 wt. % based on the total weight of the emulsion.

d. Emulsification System

The sprayable emulsion also includes an emulsification system. The emulsification system can include one or more emulsifiers to help create a stable, substantially homogeneous, uniform dispersion of the propellant and the active agent particles by preventing the separation of the sprayable emulsion into constituent phases. The emulsification system may include one or more nonionic, anionic, and/or amphoteric emulsifiers, including mixtures containing different species or mixtures of different surfactants within the same species. In one particular embodiment, the emulsification system includes one or more nonionic emulsifiers.

Nonionic surfactants, which typically have a hydrophobic base (e.g., long chain alkyl group or an alkylated aryl group) and a hydrophilic chain (e.g., chain containing ethoxy and/or propoxy moieties), can be particularly suitable. Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglycerides, or diglycerides of long chain alcohols, and mixtures thereof. Particularly suitable nonionic emulsifiers may include ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid esters (e.g., sold under the trade name TWEEN®), and sorbitan fatty acid esters (e.g., sold under the trade name SPAN™ or ARLACEL®), etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 12 to 14 carbon atoms.

Although any emulsifier may generally be employed, the present inventors have discovered that a certain combination of hydrophilic and lipophilic nonionic emulsifiers is particularly effective in stabilizing the emulsion. As is known in the art, the relative hydrophilicity or lipophilicity of an emulsifier can be characterized by the hydrophilic/lipophilic balance ("HLB") scale, which measures the balance between the hydrophilic and lipophilic solution tendencies of a compound. The HLB scale ranges from 0.5 to approximately 20, with the lower numbers representing highly lipophilic tendencies and the higher numbers representing highly hydrophilic tendencies. Desirably, the emulsion of the present invention can include at least one "hydrophilic" emulsifier that has an HLB value of from about 10 to about 20, in some embodiments from about 12 to about 19, and in some embodiments, from about 14 to about 18. Likewise, the emulsion can also include at least one "lipophilic" emulsifier that has an HLB value of from about 0.5 to about 10, in some embodiments from about 1 to about 9, and in some embodiments, from about 2 to about 8. If desired, two or more surfactants may be employed that have HLB values either below or above the desired value, but together have an average HLB value within the desired range. Regardless, the present inventors have discovered that the weight ratio of lipophilic emulsifiers to hydrophilic emulsifiers in the sprayable emulsion is typically within a range of from about 5 to about 30, in some embodiments from about 7.5 to about 25, and in some embodiments, from about 10 to about 20. Further, the present inventors have discovered that the overall HLB value of the sprayable emulsion is generally lipophilic and ranges from about 2 to about 12, such as from about 3 to about 10, such as from about 4 to about 9, such as from about 5 to about 8.

One particularly useful group of "lipophilic" emulsifiers are sorbitan fatty acid esters (e.g., monoesters, diester, triesters, etc.) prepared by the dehydration of sorbitol to give 1,4-sorbitan, which is then reacted with one or more equivalents of a fatty acid. The fatty-acid substituted moiety can be further reacted with ethylene oxide to give a second group of surfactants. The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,g-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. Such surfactants are commercially available under the name SPAN™ or ARLACEL™, usually with a letter or number designation which distinguishes between the various mono-, di- and triester substituted sorbitans. SPAN™ and ARLACEL™ surfactants are lipophilic and are generally soluble or dispersible in oil, but not generally soluble in water. One particularly suitable surfactant is sorbitan oleate, which is commercially available as SPAN™ 80. Generally these surfactants will have HLB value in the range of 1.8 to 8.6.

Other useful lipophilic emulsifiers that can be used can include, for example, silicone water-in-oil emulsifiers. By silicone it is meant a molecule that includes at least one siloxane (—Si—O—) repeating unit and further includes a hydrophobic moiety and a hydrophilic moiety. The HLB value of the silicone water-in-oil emulsifier is relatively low. For example, in some embodiments, the silicone emulsifier can have an HLB value in the range of 2 to 9.

Examples of suitable silicone water-in-oil emulsifiers can include non-crosslinked dimethicone copolyols such as alkoxy dimethicone copolyols, silicones having pendant hydrophilic moieties such as linear silicones having pendant polyether groups, branched polyether and alkyl modified silicones, branched polyglycerin and alkyl modified silicones, and combinations thereof. Examples of commercially available non-crosslinked dimethicone copolyols include the following from Dow Corning of Midland, Mich.: cyclopentasiloxane and PEG/PPG-18/18 dimethicone available as DC 5225C, and cyclopentasiloxane and PEG-12 dimethicone crosspolymer available as DC9011. Certain non-crosslinked dimethicone copolyols are cetyl dimethicone copolyols such as cetyl PEG/PPG-10/1 dimethicone sold under the name ABIL™ EM-90, branched polyether and alkyl modified silicones such as lauryl PEG-9 polydimethylsiloxyethyl dimethicone sold under the name KF-6038, and branched polyglycerin and alkyl modified silicones such as lauryl polyglyceryl-3 polydimethylsiloxyethyl dimethicone sold under the name KF-6105. Other non-crosslinked dimethicone copolyols include, for example, bis-PEG/PPG-14/ dimethicone copolyol sold under the name ABIL™ EM-97 and the polyglyceryl-4 isostearate/cetyl dimethicone copolyol/hexyl laurate mixture sold under the name ABIL™ WE 09. ABIL™ EM-90, ABIL™ EM-97, and ABIL™ WE 09 are available from Evonik Goldschmidt GmbH of Essen, Germany. KF-6038 are KF-6105 are available from Shin-Etsu Silicones of Akron, Ohio. One particularly suitable emulsifier for use in the present invention is ABIL™ WE 09, which has an HLB value of about 5. Another particularly suitable emulsifier is ABIL™ EM 90, which also has an HLB value of about 5.

Still another suitable nonionic lipophilic emulsifier that can be included in the sprayable emulsion of the present invention is octyldodecanol/octyldechyl xyloside/PEG-30, which is commercially available from Seppic S.A. under the name EASYNOV™.

Meanwhile, sorbitan fatty acid esters (e.g., monoesters, diester, triesters, etc.) that have been modified with polyoxyethylene are likewise a particularly useful group of "hydrophilic" emulsifiers. These materials are typically prepared through the addition of ethylene oxide to a 1,4-sorbitan ester. The addition of polyoxyethylene converts the lipophilic sorbitan ester surfactant to a hydrophilic surfactant that is generally soluble or dispersible in water. Such materials are commercially available under the designation TWEEN™ (e.g., TWEEN™ 80, polysorbate 80, or polyethylene (20) sorbitan monooleate). TWEEN™ surfactants generally have a HLB value in the range of 9.6 to 16.7. For instance TWEEN™ 80 has an HLB value of 15. Still other suitable hydrophilic emulsifiers can include sucrose fatty acid esters, such as saccharose monopalmitate (HLB of 15) and saccharose monostearate (HLB of 11), or PEG-32 glyceryl laurate (HLB of 14), as well as polyethylene glycol (PEG) n-alkanol esters of the BRIJ™ family such as BRIJ™ 35, 56, 58, 76, 78, and 99, which have an HLB in the range of 12.4 to 16.9. BRIJ™ 56 is polyoxyethylene[10] cetyl ether, for example, has an HLB value of 12.9.

Regardless of the particular emulsifiers utilized in the emulsification system, the emulsification system can be present in the sprayable emulsion in an amount ranging from about 0.1 wt. % to about 20 wt. %, such as from about 0.5 wt. % to about 15 wt. %, such as from about 1 wt. % to about 10 wt. % based on the total weight of the emulsion. Further, the present inventors have discovered that the weight ratio of lipophilic emulsifiers to hydrophilic emulsifiers in the emulsification system component of the sprayable emulsion is typically within a range of from about 5 to about 30, in some embodiments from about 7.5 to about 25, and in some embodiments, from about 10 to about 20.

e. Viscosity Modifier

In addition, the emulsion can include one or more viscosity modifiers which can also help to prevent the separation of the various components of the emulsion. For instance, in some embodiments, the one or more viscosity modifiers can be added to the oil phase or the water phase of an emulsion to adjust the viscosity such that separate components in the emulsion are more miscible. Further, the viscosity of the overall emulsion can be adjusted so that it is not so high that the emulsion cannot be sprayed onto a surface, but it is not so low that the emulsion is too runny such that it does not evenly coat the surface. As such, the emulsion can have a viscosity ranging from about 500 centipoise to about 10,000 centipoise, such as from about 1000 centipoise to about 8000 centipoise, such as from about 1500 centipoise to about 6000 centipoise, such as from about 2000 centipoise to about 4000 centipoise.

When a water-in-oil emulsion or an oil-in-water emulsion is formed, the one or more viscosity modifiers can be added to the water phase of the water-in-oil emulsion or the oil-in-water emulsion to enhance the miscibility between the water phase and the oil phase, which promotes the substantially homogeneous distribution of the components of the sprayable emulsion. It is also to be understood, however, that the viscosity modifier can be added to an already-formed oil-in-water or water-in-oil emulsion to adjust the viscosity as needed.

Suitable viscosity modifiers include carboxylic acid polymers which are crosslinked compounds containing one or more monomers derived from acrylic acid, substituted acrylic acids, and salts and derivatives of these acrylic acids and substituted acrylic acids. They can be crosslinked homopolymers of an acrylic acid or of a derivative thereof, such as acrylamidopropylsulfonic acid. They can be also crosslinked copolymers having (i) a first monomer selected from the group consisting of (meth)acrylic acid, derivatives thereof, short chain (i.e., $C_1$-$C_4$) acrylate ester monomers, and mixtures thereof, and (ii) a second monomer which is a long chain (i.e., $C_8$-$C_{40}$) substituted polyethylene glycol acrylate ester monomer.

Examples of commercially available carboxylic acid polymers include CARBOPOL™ 1342, PEMULEN™ TR-1, and PEMULEN™ TR-2 available from Lubrizol Corp.; Sepigel 305, SIMULGEL™ EG, SIMULGEL™ NS, and SIMULGEL™ 600, available from Seppic S.A.; VISCOLAM™ AT100P and VISCOLAM™ AT64/P, available from Lamberti S.p.A. One commercially available viscosity modifier is available from Seppic S.A. as SIMULGEL™ NS. SIMULGEL™ NS includes a hydroxylethyl acrylate/sodium acryloyldimethyl taurate copolymer, squalane, and polysorbate 60, which can be added to an oil phase of a water-in-oil or oil-in-water emulsion.

Other suitable viscosity modifiers that can be used include cornstarch (topical starch), talc, rice starch, oat starch, tapioca starch, potato starch, legume starches, soy starch, turnip starch, microcrystalline cellulose, kaolin, aluminum starch octenyl succinate, and mixtures thereof. Water soluble aluminum starch octenyl succinates are commercially available from National Starch & Chemical Co. as DRY FLO™ Pure, DRY FLO™ XT, DRY FLO™ PC, and/or DRY FLO™ AF (aluminum free grade) and are water soluble such that they can be included in a water phase of a water-in-oil emulsion or an oil-in-water emulsion.

Regardless of the particular viscosity modifiers utilized, the viscosity modifier can be present in the sprayable emulsion in an amount ranging from about 0.05 wt. % to about 15 wt. %, such as from about 0.1 wt. % to about 10 wt. %, such as from about 0.5 wt. % to about 5 wt. % based on the total weight of the sprayable emulsion.

f. Conditioning Agents

The sprayable emulsion can further include one or more conditioning agents to help condition the skin. For example, the sprayable emulsion can include thymol iodide, sodium chloride, magnesium dichloride, magnesium sulfate, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols, ricinoleate, acetate of ethoxylated alcohols-esters, hydrogenolysis of lanolin, ethoxylated hydrogenated lanolin, ethoxylated sorbitol lanolin, or a combination thereof. Thymol iodide and magnesium sulfate may be particularly useful. One or more conditioning agents can be present in the sprayable emulsion in an amount ranging from about 0.05 wt. % to about 10 wt. %, such as from about 0.1 wt. % to about 7.5 wt. %, such as from about 0.5 wt. % to about 5 wt. % based on the total weight of the emulsion.

g. Additional Components

Other optional components in the sprayable emulsion can include skin care-additives such as emollients; as well as fragrances and preservatives. For instance, an emollient such as caprylic/capric triglyceride can be included in the sprayable emulsion. Other suitable emollients include stearoxy trimethyl silane, cetyl lactate, and alkyl lactate, such as $C_{12}$-$C_{15}$ alkyl lactate. When emollients are used, the sprayable emulsion can feel smooth to the touch when applied to the skin. One or more emollients can be present in the sprayable emulsion in an amount ranging from about 0.1 wt. % to about 25 wt. %, such as from about 0.5 wt. % to about 20 wt. %, such as from about 1 wt. % to about 15 wt. % based on the total weight of the sprayable emulsion.

Further, a fragrance can be present in the sprayable emulsion in an amount ranging from about 0.005 wt. % to about 2 wt. %, such as from about 0.01 wt. % to about 1.5 wt. %, such as from about 0.02 wt. % to about 1 wt. % based on the total weight of the sprayable emulsion.

Meanwhile, preservatives can be present in the sprayable emulsion in an amount ranging from about 0.01 wt. % to about 6 wt. %, such as from about 0.02 wt. % to about 4 wt. %, such as from about 0.05 wt. % to about 1 wt. % based on the total weight of the emulsion. Suitable preservatives include paraben-based preservatives such as methylparaben and propylparaben.

In addition, the present inventors have found that a freezing point depressant can be included in the emulsion to limit the amount of crystallization of any solid components, which can then reduce or limit clogging of the emulsion when sprayed. If desired, one or more freezing point depressants may be employed, such as glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); and so forth. Such freezing point depressants can be present in the emulsion in an amount ranging from about 0.1 wt. % to about 15 wt. %, such as from about 0.5 wt. % to about 10 wt. %, such as from about 1 wt. % to about 5 wt. % based on the total weight of the emulsion.

II. Formation of the Sprayable Emulsion

Generally, the sprayable emulsion of the present invention can be made by forming a base emulsion, then introducing the base emulsion composition into a spray container, followed by injecting a propellant into the container. When the base emulsion composition is in the form of a water-in-oil emulsion or an oil-in-water emulsion, for example, the base emulsion composition can be made by first separately forming an oil phase and a water phase.

The manner in which the emulsion is formed may vary as is known to those skilled in the art. In one embodiment, for example, an oil phase is formed by blending one or more oils with one or more components of the emulsification system described above. However, it is also be understood that one or more of the components of the emulsification system can be added to the water phase in another embodiment. Emollients, conditioning agents, etc. also be added to form the oil phase. In such embodiments, the oil phase can contain oils in an amount of from about 30 wt. % to about 80 wt. %, such as from about 35 wt. % to about 70 wt. %, such as from about 40 wt. % to about 60 wt. % based on the total weight of the oil phase. Further, the oil phase can include emulsifiers in an amount ranging from about 5 wt. % to about 35 wt. %, such as from about 10 wt. % to about 30 wt. %, such as from about 15 wt. % to about 25 wt. % based on the total weight of the oil phase. The addition of the emulsifiers can result in an oil phase having an HLB value between about 6 and about 7. In addition, the oil phase can include emollients in an amount ranging from about 10 wt. % to about 45 wt. %, such as from about 15 wt. % to about 40 wt. %, such as from about 20 wt. % to about 35 wt. % based on the total weight of the oil phase. Moreover, the oil phase can include conditioning agents in an amount ranging from about 0.5 wt. % to about 10 wt. %, such as from about 1 wt. % to about 7.5 wt. %, such as from about 1.5 wt. % to about 5 wt. % based on the total weight of the oil phase.

Meanwhile, the water phase can be formed by blending water and any water soluble components of the sprayable emulsion, such as conditioning agents, viscosity modifiers, emulsifiers, etc. However, it is also to be understood that the water phase may include only water in other embodiments. As such, the water phase can include water in an amount ranging from about 50 wt. % to about 100 wt. %, such as from about 55 wt. % to about 99 wt. %, such as from about 60 wt. % to about 98 wt. %. The water phase can also include conditioning agents in an amount ranging from about 0.5 wt. % to about 15 wt. %, such as from about 1 wt. % to about 10 wt. %, such as from about 1.5 wt. % to about 7.5 wt. % based on the total weight of the water phase. Additionally, the water phase can include viscosity modifiers in an amount ranging from about 0.25 wt. % to about 10 wt. %, such as from about 0.5 wt. % to about 7.5 wt. %, such as from about 1 wt. % to about 5 wt. % based on the total weight of the water phase.

After the oil phase and water phase are separately formed, the water phase can be added to the oil phase to form a water-in-oil emulsion. The combination of the phases may be facilitated through agitation (e.g., stirring) and control of the temperatures of each mixture. Next, the active agent particles can be added to the water-in-oil emulsion. The active agent particles can be present in the water-in-oil emulsion in an amount ranging from about 0.25 wt. % to about 35 wt. %, such as from about 0.5 wt. % to about 30 wt. %, such as from about 1 wt. % to about 25 wt. %, such as from about 5 wt. % to about 15 wt. % based on the total weight of the base emulsion composition.

Then, if desired, other components such as fragrances, preservatives, freezing point depressants, and additional viscosity modifiers can be added to the emulsion. Fragrances can be added in an amount ranging from about 0.01 wt. % to about 5 wt. %, such as from about 0.05 wt. % to about 2.5 wt. %, such as from about 0.1 wt. % to about 1 wt. % based on the total weight of the base emulsion composition. Likewise, preservatives can be added in an amount ranging from about 0.01 wt. % to about 5 wt. %, such as from about 0.05 wt. % to about 2.5 wt. %, such as from about 0.1 wt. % to about 1 wt. % based on the total weight of the base emulsion composition. In addition, freezing point depressants can be added in an amount ranging from about 0.5 wt. % to about 15 wt. %, such as from about 1 wt. % to about 10 wt. %, such as from about 2 wt. % to about 8 wt. % based on the total weight of the base emulsion composition. Further, viscosity modifiers can be added in an amount ranging from about 0.1 wt. % to about 15 wt. %, such as from about 0.5 wt. % to about 10 wt. %, such as from about 1 wt. % to about 8 wt. % based on the total weight of the base emulsion composition. As such, it is to be understood that in some embodiments, a first viscosity modifier can be added during formation of the water phase, while a second viscosity modifier can be added after forming the emulsion by combining the water and oil phases to form the base emulsion composition.

Regardless of which phase is being formed, the temperature can range from about 15° C. to about 40° C., such as from about 18° C. to about 35° C., such as from about 20° C. to about 30° C. After the separate phases are mixed as described above, the resulting base emulsion composition can then be filled into a spray container, such as an aerosol spray container. The container can then be sealed, after which the propellant can be introduced into the container, such as via a valve. The container can be filled with the propellant at a pressure ranging from about 130 psi to about 230 psi, such as from about 140 psi to about 220 psi, such as from about 150 psi to about 210 psi.

III. Spray Delivery System

Various aerosol spray containers can be used in conjunction with the sprayable emulsion to form a system for spraying the emulsion onto a surface such as skin. One embodiment of a spray delivery system contemplated by the present invention is described with reference to FIG. 1. The spray delivery can include a spray container 101 formed of metal or reinforced plastic. The spray container 101 has an upper opening into which a spray head 102 is fitted. The spray head or 102 is fixed onto the spray container 101 in such a manner that a flange 104 of the spray head is connected to a collar 103 formed around the edge of the upper opening in the spray container 101 by welding or other possible joining methods. This results in an airtight connection between the spray head 102 and spray container 101.

The spray head 102 is provided with a valve 105 that is retained by the flange 104. The valve 105 is kept closed in its normal condition by the energizing force of a spring 106, but it opens when the spray head 102 is pressed. The spray head 102 further has a spray nozzle 107 which communicates with the valve 105 through a conduit pipe 108. Meanwhile, a dip tube 109 is connected to the valve 105 and extends to the bottom of the spray container 101. By pressing the spray head 102 downwardly against the spring 106, the valve 105 opens to form a fluid passage from the lower end port of the dip tube 109 to the spray nozzle 107 through the valve 105 and conduit pipe 108.

A sprayable emulsion 110, formed as discussed above, can be charged into the spray container 101. Then, by pressing the spray head 102, the sprayable emulsion is discharged in the form of a fine mist from the spray nozzle 107 through the aforementioned fluid passage by the pressure associated with the propellant that is substantially homogeneously dispersed in the sprayable emulsion 110.

Another embodiment of a spray delivery system is described with reference to FIGS. 2A, 2B, 3 and 4. Because of the use of active agent particles, it is possible that the sprayable emulsion could clog some spray delivery systems. For instance, standard aerosol spray delivery systems often utilize an actuator (spray button) not intended for delivering compositions containing high concentrations of particulate material such as the active agent particles of the present invention. Such actuators often utilize a mechanical break-up insert to finely atomize sprayable emulsions containing low levels of particulates. For instance, the actuators can contain small channels to cause a swirling effect, resulting in a fine mist spray. However, when sprayable compositions and emulsions containing higher amounts of active agent particles are utilized, the active agent particles or any other particles can clog the actuator and prevent an even spray from the container. As such, the spray delivery system of the present invention represented by FIGS. 2A, 2B, 3 and 4 does not include the aforementioned actuator channels and is free from a mechanical break-up insert. Instead, the spray delivery system utilizes a valve and stem system where the stem design allows for automatic wiping of the stem inside the valve as the valve is sprayed, which prevents the buildup of solids inside the valve, thus minimizing the risk of clogging. In addition, the valve includes a valve orifice having a diameter that is large enough such that the active agent particles and other particles of the sprayable emulsion do not clog inside the container and such that an even mist can be achieved. Further, the valve includes a vapor tap to allow for enhanced blending of the propellant vapor during spraying and to prevent the buildup of particles inside the valve. The addition of the vapor tap also results in a more uniform delivery of the sprayable emulsion from the delivery system. The vapor tap also allows for an increased weight percentage of propellant to be utilized, which helps to create a drier, less runny product when delivered to the surface of the skin. Further, the vapor tap creates a spray that feels warmer because it helps to volatilize the propellant and solvents before the emulsion reaches the surface of the skin.

The spray system is discussed in more detail below in reference to FIGS. 2A, 2B, 3, and 4. FIG. 2A shows a front view of a non-mechanical breakup actuator 200 that can be used in a spray delivery system according to one embodiment of the present disclosure. The actuator 200 is a component that can be used to depress a stem component of a valve assembly to initiate introduction of the sprayable emulsion, as is discussed in more detail below in reference to FIGS. 3 and 4. The actuator 200 includes a locking ring 201, an insert 202, and a dome 203. The locking ring 201 keeps the actuator from being depressed inadvertently. The actuator dome 203 can contain the insert 202, and the insert 202 can determine the spray characteristics of the sprayable emulsion. The insert 202 of FIGS. 2A and 2B is a non-mechanical breakup insert. The insert 202 defines an opening 204 from which the sprayable emulsion of the present invention can exit the actuator, and the opening is hereinafter referred to as the actuator orifice or exit orifice 204. The exit orifice 204 can have a diameter selected based on the particle size of the particulate components in the sprayable emulsion, such as the active agent particles, so that the particles and other components of the sprayable emulsion can be sprayed from the exit orifice 204 without causing clogging of the spray delivery system. Further, by selectively controlling the diameter of the exit orifice 204, the size of the resulting spray pattern can also be influenced. For instance, too small of a diameter can result in a very narrow spray pattern, while too large of a diameter can result in a spray pattern that is too wide, resulting in overspray into the surrounding environment other than the surface to be sprayed, such as clothing, bedding, etc.

For instance, the exit orifice 204 can have a diameter ranging from about 0.3 millimeters to about 0.6 millimeters, such as from about 0.35 millimeters to about 0.55 millimeters, such as from about 0.4 millimeters to about 0.5 millimeters. FIG. 2B is a cross-sectional side view of the actuator of FIG. 2A, which shows the arrangement of the exit orifice 204 in relation to the insert 202 positioned inside the dome 203. The exit orifice is connected to a stem 302 of a valve assembly via an exit path 205, which is discussed in more detail in FIG. 3.

Turning now to FIGS. 3 and 4, a cross-sectional side view of a spray delivery system that includes a spray valve assembly 300 and mounting cup 301 that can be used in conjunction with the actuator 200 of FIGS. 2A and 2B is shown. The actuator 200 is connected to the valve assembly 300 by exit path 205 as shown in FIG. 2B. The spray valve assembly 300 includes a housing or body 305 that holds the stem 302, a stem gasket 304, and a spring 307. A dip tube 311 is also attached to the housing 305 via a tail pipe 309. The mounting cup 301 holds the spray valve assembly 300 together and can be crimped onto a container 401 to provide a seal. Generally, when the actuator 203 (see FIGS. 2A and 2B), which is disposed above the mounting cup 301, is depressed against the spring 307, the stem 302 of the valve assembly 300 moves downward, opening the seal between the stem gasket 303 and stem 302, such that a stem orifice 303 in the stem 302 passes below the stem gasket 304. This results in the propellant component of the sprayable emulsion forcing the base emulsion composition up the dip tube 311 through a tailpipe orifice 310, into the valve body 305. A vapor tap 306 formed in the valve body 305 supplies additional propellant to the valve body 305 and helps to mix the liquid base emulsion composition and propellant in the valve body 305, which can result in a more homogeneous distribution and reduce the risk of clogging of any active agent particles. The vapor tap 306 also keeps the base emulsion composition out of the valve body 305 when at rest due to the vapor pushing the base emulsion composition down, and also functions to prevent product settling. Once the sprayable emulsion (i.e., the substantially homogeneously blended propellant and base emulsion composition) reaches the stem through the stem orifice 303, it then passes through the exit path 205, and out the exit orifice 204 as a fine mist that does not clog the spray delivery system 400.

The dimensions of the various components can be selected to further minimize the risk of clogging. For instance, the stem 302 can have a diameter of from about 3 millimeters to about 5.5 millimeters, such as from about 3.5 millimeters to about 5 millimeters, such as from about 4 millimeters to about 4.5 millimeters. Meanwhile, the stem orifice 303 can have a diameter of from about 0.5 millimeters to about 0.75 millimeters, such as from about 0.55 millimeters to about 0.7 millimeters, such as from about 0.6 millimeters to about 0.65 millimeters. Additionally, the tailpiece orifice 310 can have a diameter of from about 0.75 millimeters to about 2 millimeters, such as from about 1 millimeter to about 1.75 millimeters, such as from about 1.25 millimeters to about 1.5 millimeters. Further, the vapor tap 306 can have a diameter of from about 0.1 millimeters to about 0.5 millimeters, such as from about 0.15 millimeters to about 0.45 millimeters, such as from about 0.2 millimeters to about 0.4 millimeters. By selectively controlling the aforementioned dimensions, the propellant of the sprayable emulsion can remain substantially homogeneously distributed throughout the emulsion to reduce settling of the active agent particles, and the sprayable emulsion can leave the exit orifice 204 as a fine mist with less fly away and can be more evenly distributed than when, for instance, a mechanical actuator is utilized.

IV. Application of the Sprayable Emulsion

As a result of the combination of the type of spray delivery system utilized and the characteristics of the sprayable emulsion, a substantially uniform coating of the emulsion can be applied to a surface. For instance, the emulsion of the present invention can be applied to a surface of the skin for the treatment of various skin conditions or irritations such as diaper rash; dry skin; ulcers; superficial cuts, scrapes, wounds, and first degree burns; etc. Areas of skin that can be treated include the buttocks, particularly in the case of diaper rash/incontinent dermatitis, as well as the arms, elbows, hands, abdomen, back, sacrum, coccyx, hips, knees, feet, ankles, heels, etc. As the emulsion reaches the skin's surface, the propellant can evaporate, leaving a substantially uniform coating of the active agent particles on the skin. Further, the active agent particles can be distributed throughout the coating in a substantially uniform manner. After the emulsion has been sprayed onto the skin in the form of a substantially uniform coating, the amount of active agent particles present in the emulsion on the skin can range from about 0.25 wt. % to about 35 wt. %, such as from about 0.5 wt. % to about 30 wt. %, such as from about 1 wt. % to about 25 wt. %, such as from about 5 wt. % to about 15 wt. % based on the total weight of the resultant coating (e.g., the sprayable emulsion excluding the evaporated components such as the propellant).

The present invention may be better understood by reference to the following examples.

Example 1

A sprayable emulsion was formed from a base emulsion composition including a preservative phase, an oil phase, a water phase, and active agent particles, to which a propellant was added. First, to make the preservative phase of the base emulsion composition, a freezing point depressant was added to a beaker and agitated with a propeller. Next, preservatives were added to the beaker and mixing was initiated using a stirrer equipped with an anchor-type side-wipe agitator. Agitation was continued for at least 15 minutes until the solution was completely dissolved. The preservative phase was then set aside.

Next, to make the oil phase of the base emulsion composition, emollients were added to a separate beaker and agitated with a propeller to initiate mixing while maintaining a temperature between 20° C. and 23° C., after which the polyglyceryl-4 isostearate/cetyl dimethicone copolyol/hexyl laurate emulsifier was added, followed by the cetyl PEG/PPG-10/1 dimethicone emulsifier, the sorbitan oleate emulsifier, the polysorbate 80 emulsifier, and the octyldodecanol/octyldechyl xyloside/PEG-30 emulsifier. Mixing via agitation was continued, while maintaining a temperature between 20° C. and 25° C. Next, the silicone oil was added to the beaker, while maintaining a temperature between 20° C. and 23° C. A homogenizer was then used for agitation, using cooling water to maintain a temperature between 20° C. and 25° C., after which a conditioning agent was added. Agitation was continued for at least 15 minutes until the solution was completely dissolved, maintaining a temperature between 20° C. and 28° C. The resulting oil phase of the base emulsion composition had an HLB value between 6 and 7.

Next, the water phase of the base emulsion composition was prepared in a separate beaker. Water was added to the beaker while maintaining a temperature between 20° C. and 28° C. Mixing was initiated using a stirrer equipped with a stainless steel three propeller blade. A water-soluble conditioning agent was added to the beaker and mixing was continued for at least 15 minutes until all solids were dissolved. Then, the viscosity modifier containing hydroxyethyl acrylate/sodium acryloyldimethyl taurate copolymer, squalane, and polysorbate 60 was added to the beaker, and mixing was continued for at least 15 minutes.

To prepare the base emulsion composition, the oil phase beaker was maintained at a temperature between 20° C. and 25° C. The water phase was then slowly transferred to the oil phase beaker under homogenizer agitation, where the transfer time was at least 20 minutes. The homogenizer speed was increased as needed, while maintaining a temperature between 20° C. and 25° C. The resulting water-in-oil emulsion was then covered and mixed for at least 30 minutes. The preservative phase was then added to the beaker while continuing mixing for at least 15 minutes and maintaining a temperature of from 20° C. to 25° C. After ensuring that all powders were off the surface and increasing the mixing speed as needed, zinc oxide particles were added under homogenizer agitation and mixed for at least 5 minutes, increasing the speed as needed and maintaining a temperature of from 20° C. to 25° C. Then the viscosity modifier aluminum starch octenylsuccinate was added under homogenizer agitation and mixed for at least 5 minutes, increasing the speed as needed and maintaining a temperature of from 20° C. to 25° C. Thereafter, fragrance was added to the beaker under homogenizer agitation, and the emulsion was mixed for at least 15 minutes. The resulting base emulsion composition had an HLB value of 7.42.

After the base emulsion composition was formed, it was filled into an aerosol spray container, after which the container's valve was sealed or crimped to the top of the container. Then, HFO-1234ze propellant was pressure filled via the valve into the container at a pressure of about 200 pounds. The resulting sprayable emulsion included a substantially homogeneous blend of the propellant and active agent particles, and contained 22 wt. % of the propellant and 78 wt. % of the base emulsion composition. The sprayable emulsion had a specific gravity of about 1.045. The weight percentages of the components used in the sprayable emulsion are summarized below in Table 1. Once sprayed on a surface (e.g., skin) as a substantially uniform coating, the emulsion contained 10.4 wt. % of zinc oxide particles due to evaporation of the propellant.

TABLE 1

| Sprayable Emulsion Components Sprayable Emulsion | |
|---|---|
| Component | Wt. % |
| HFO-1234ze | 22.00 |
| Zinc Oxide Particles | 8.11 |
| Polyglyceryl-4 Isostearate; Cetyl PEG/PPG-10/1 Dimethicone; Hexyl Laurate | 0.98 |
| Cetyl PEG/PPG-10/1 Dimethicone | 0.98 |
| Sorbitan Oleate | 0.43 |
| Polysorbate 80 | 0.35 |
| Octyldodecanol/Octyldodecyl Xyloside/PEG-30 Dipolyhydroxystearate | 3.12 |
| Aluminum Starch Octenylsuccinate | 2.34 |
| Hydroxyethyl Acrylate/Sodium Acryloyldimethyl Taurate Copolymer, Squalane, Polysorbate 60 | 0.78 |
| Silicone Oil | 15.60 |
| Water | 29.76 |
| Conditioning Agents | 1.95 |
| Fragrance | 0.16 |
| Freezing Point Depressant | 3.12 |
| Preservatives | 0.20 |
| Emollients | 10.14 |
| Total | 100.00 |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A sprayable emulsion comprising a hydrofluoro-based propellant, an emulsification system, an oil phase, a water phase, and active agent particles, wherein the emulsification system comprises at least one nonionic emulsifier, wherein the emulsion has a viscosity ranging from about 500 centipoise to about 10,000 centipoise and a hydrophilic to lipophilic balance (HLB) value of from about 2 to about 12, wherein the emulsification system comprises a nonionic lipophilic emulsifier and a nonionic hydrophilic emulsifier, wherein the nonionic lipophilic emulsifier comprises a non-crosslinked dimethicone polyol, a sorbitan fatty acid ester, and an octyldodecanol, and wherein the nonionic hydrophilic emulsifier comprises a sorbitan fatty acid ester modified with a polyoxyethylene.

2. The sprayable emulsion of claim 1, wherein the weight ratio of the nonionic lipophilic emulsifiers to the nonionic hydrophilic emulsifiers ranges from about 5 to about 30.

3. The sprayable emulsion of claim 1, wherein the propellant is homogeneously distributed throughout the emulsion.

4. The sprayable emulsion of claim 1, wherein the active agent particles are homogeneously distributed throughout the emulsion.

5. The sprayable emulsion of claim 1, wherein the propellant is present in an amount ranging from about 5 wt. % to about 95 wt. % and the active agent particles are present in an amount ranging from about 0.5 wt. % to about 30 wt. % based on the total weight of the emulsion.

6. The sprayable emulsion of claim 1, wherein the emulsion is a water-in-oil emulsion.

7. The sprayable emulsion of claim 1, wherein the oil phase comprises from about 1 wt. % to about 35 wt. % and the water phase comprises from about 1 wt. % to about 50 wt. % of the total weight of the emulsion.

8. The sprayable emulsion of claim 1, wherein the oil phase comprises a silicone oil.

9. The sprayable emulsion of claim 1, wherein the water phase comprises water.

10. The sprayable emulsion of claim 1, wherein water is present in an amount of less than about 50 wt. % based on the total weight of the emulsion.

11. The sprayable emulsion of claim 1, wherein the emulsion further comprises a viscosity modifier.

12. The sprayable emulsion of claim 11, wherein the viscosity modifier comprises a carboxylic acid polymer, a starch, or a combination thereof.

13. The sprayable emulsion of claim 1, wherein less than about 3 wt. % of the active agent particles in the emulsion settle when the emulsion is stored in a container at about 21° C. for 3 days.

14. The sprayable emulsion of claim 1, wherein the propellant has a first specific gravity and the sprayable emulsion has a second specific gravity, wherein the ratio of the first specific gravity to the second specific gravity is from about 0.7 to about 1.6.

15. The sprayable emulsion of claim 1, wherein the propellant has a vapor pressure of less than about 60 psi at about 21° C.

16. The sprayable emulsion of claim 1, wherein the propellant comprises a hydrofluoro-olefin or a hydrofluoro-alkane.

17. The sprayable emulsion of claim 1, wherein the active agent particles comprise a moisture barrier, antifungal, antibacterial, analgesic, antiseptics, anesthetic, anti-inflammatory, antipruritic, or a combination thereof.

18. The sprayable emulsion of claim 1, wherein the emulsion further comprises one or more emollients, conditioning agents, freezing point depressants, preservatives, or a combination thereof.

19. A method of forming a sprayable emulsion comprising:
    forming a base emulsion composition, wherein the base emulsion composition comprises active agent particles, an emulsification system, an oil phase, and a water phase, wherein the emulsification system comprises at least one nonionic emulsifier;
    introducing the base emulsion composition into a spray container; and
    injecting a hydrofluoro-based propellant into the container, wherein the sprayable emulsion has a viscosity of from about 500 centipoise to about 10,000 centipoise and a hydrophilic to lipophilic balance (HLB) value of from about 2 to about 12, wherein the emulsification system comprises a nonionic lipophilic emulsifier and a nonionic hydrophilic emulsifier, wherein the nonionic lipophilic emulsifier comprises a non-crosslinked dimethicone polyol, a sorbitan fatty acid ester, and an octyldodecanol, and wherein the nonionic hydrophilic emulsifier comprises a sorbitan fatty acid ester modified with a polyoxyethylene.

20. The method of claim 19, wherein the weight ratio of the nonionic lipophilic emulsifiers to the nonionic hydrophilic emulsifiers ranges from about 5 to about 30.

21. The method of claim 19, wherein the emulsification system is added to the oil phase.

22. The method of claim 19, wherein the base emulsion system further comprises a viscosity modifier.

23. The method of claim 22, wherein the viscosity modifier comprises a carboxylic acid polymer, a starch, or a combination thereof.

24. The method of claim 22, wherein the viscosity modifier is added to the water phase.

25. The method of claim 19, wherein the active agent particles are substantially homogeneously dispersed throughout the sprayable emulsion.

26. The method of claim 19, wherein the propellant is substantially homogeneously dispersed throughout the sprayable emulsion.

27. The method of claim 19, further comprising adding one or more preservatives, emollients, skin conditioners, freezing point depressants, or a combination thereof to the emulsion.

28. The method of claim 19, wherein the propellant has a first specific gravity and the sprayable emulsion has a second specific gravity, wherein the ratio of the first specific gravity to the second specific gravity is from about 0.7 to about 1.6.

29. The method of claim 19, wherein the sprayable emulsion is formed at a temperature ranging from about 15° C. to about 40° C.

* * * * *